United States Patent
Sinha et al.

(10) Patent No.: US 7,910,293 B2
(45) Date of Patent: Mar. 22, 2011

(54) DEVELOPMENT OF PROGNOSTIC MARKERS FROM THE SALIVA OF HEAD AND NECK CANCER PATIENTS

(75) Inventors: Uttam K. Sinha, Los Angeles, CA (US); Rizwan Masood, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/058,576

(22) Filed: Mar. 28, 2008

(65) Prior Publication Data

US 2009/0246761 A1    Oct. 1, 2009

Related U.S. Application Data

(60) Provisional application No. 60/908,494, filed on Mar. 28, 2007.

(51) Int. Cl.
*C12Q 1/00* (2006.01)
*G01N 33/574* (2006.01)

(52) U.S. Cl. .................. 435/4; 435/7.23; 436/64

(58) Field of Classification Search ............... None
See application file for complete search history.

(56) References Cited

U.S. PATENT DOCUMENTS

| 2005/0014165 A1* | 1/2005 | Lee et al. ................. 435/6 |
| 2005/0069963 A1* | 3/2005 | Lokshin et al. .......... 435/7.23 |
| 2005/0214880 A1  | 9/2005 | Franzmann et al. |

OTHER PUBLICATIONS

Gokhale et al, Oral Oncology vol. 41, p. 70-76, 2005.*
Linkov et al, Caner Epidemiol Biomarkers Prev 16 (1), p. 102-107, Jan. 2007.*
St. John et al, Arch Otolaryngol Head Neck Surg vol. 130, p. 929-935, 2004.*
O-charoenrat et al. "Expression of Matrix Metalloproteinases and Their Inhibitors Correlates With Invasion and Metastasis in Squamous Cell Carcinoma of the Head and Neck" Arch Otolaryngol Head Neck Surg. vol. 127, pp. 813-820, Jul. 2001.
International Search Report for corresponding PCT application PCT/US08/58698 lists the references above, 2009.

* cited by examiner

*Primary Examiner* — Misook Yu
*Assistant Examiner* — Lei Yao
(74) *Attorney, Agent, or Firm* — DLA Piper LLP (US)

(57) ABSTRACT

The present invention relates to biomarkers that are useful for the detection of cancer. The invention further relates to biomarkers and methods of using biomarkers for the early detection of head and neck cancer.

8 Claims, 1 Drawing Sheet

DEVELOPMENT OF PROGNOSTIC MARKERS FROM THE SALIVA OF HEAD AND NECK CANCER PATIENTS

The present application claims the benefit of the filing date of U.S. Provisional Application No. 60/908,494, filed Mar. 28, 2007, the disclosure of which is incorporated herein by reference in its entirety.

FIELD OF THE INVENTION

The present invention relates in general to the detection of diseases. More specifically, the invention provides biomarkers and methods of using them for the early detection of cancer.

BACKGROUND OF THE INVENTION

Head and neck squamous cell carcinoma (HNSCC) is the sixth most common cancer, with more than 900,000 cases diagnosed each year, and is one of the major causes of cancer death worldwide (Sankaranarayanan, et al., 1998). In the United States alone, 50,000 new cases and 8,000 deaths are reported each year (Greeenlee, et al., 2000). It affects the oral cavity, the oropharynx, the larynx, and the hypopharynx (Mashberg, et al., 1993). Tobacco carcinogens are believed to be the primary etiologic agents of the disease, with alcohol consumption, age, gender, and ethnic background as contributing factors (Hu, et al., 2007). There is no known inherited form of the disease, however mutations of several well documented tumor associated genes have been described in HNSCC (Zimmermann, et al., 2007; Righini, et al., 2007; Ohshiro, et al., 2007; Chai, et al., 2006; Brailo, et al., 2006).

Although surgery and radiotherapy are highly effective treatments for HNSCC early-stage disease (stage I or II), with cure rates ranging from 70% to 85%, advanced disease (stage III or IV) remains difficult to control, with an estimated 5-year survival rate of 30% to 40% (Vokes, et al., 1993). Therefore, prevention and early diagnosis of high-risk premalignant lesions are high priorities for reducing morbidity and mortality in head and neck cancer. In addition, regional metastasis is an important factor in the prognosis and choice of treatment for patients with HNSCC. The presence of nodal metastasis significantly affects the survival of the patient.

The molecular mechanisms for the progression of HNSCC cancers are not well understood but are widely believed to involve alcohol, tobacco and deregulation of growth factors leading to development of cancer (Boyle, et al., 1993 and Brachman, et al., 1994). Microarray data shows elevation of IL-8, IL-6, VEGF, MMP-9, TGF-B, MMP-7, plasminogen activated (PA), uPA, IGF and INF-2 proteins in HNSCC (unpublished data). The expression of these proteins increases as the disease progresses and thus, appears to have a direct role in the development of HNSCC. The proteins are also shown to be elevated in persons who smoke or drink heavily, but do not have HNSCC.

SUMMARY OF THE INVENTION

In one embodiment, the invention relates to biomarkers that are highly expressed in cancer.

In another embodiment, the invention relates to biomarkers that are used for the early detection of cancer.

In accordance with one embodiment, the invention relates to methods of detecting biomarkers that are highly expressed in cancer.

In accordance with another embodiment, the invention relates to methods of using biomarkers for the early detection of cancer.

To practice methods relating to the early detection of cancer, biomarker expression levels of sample biopsies from persons believed to be at risk for developing cancer are compared to the expression levels of control biopsies (normal biopsy that does not have cancer) and advanced stage cancer biopsies. If sample biomarker expressions levels are higher than normal control biomarker expression levels, but less than cancer biopsies, then cancer has been detected early.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

DETAILED DESCRIPTION OF THE INVENTION

Figure 1:
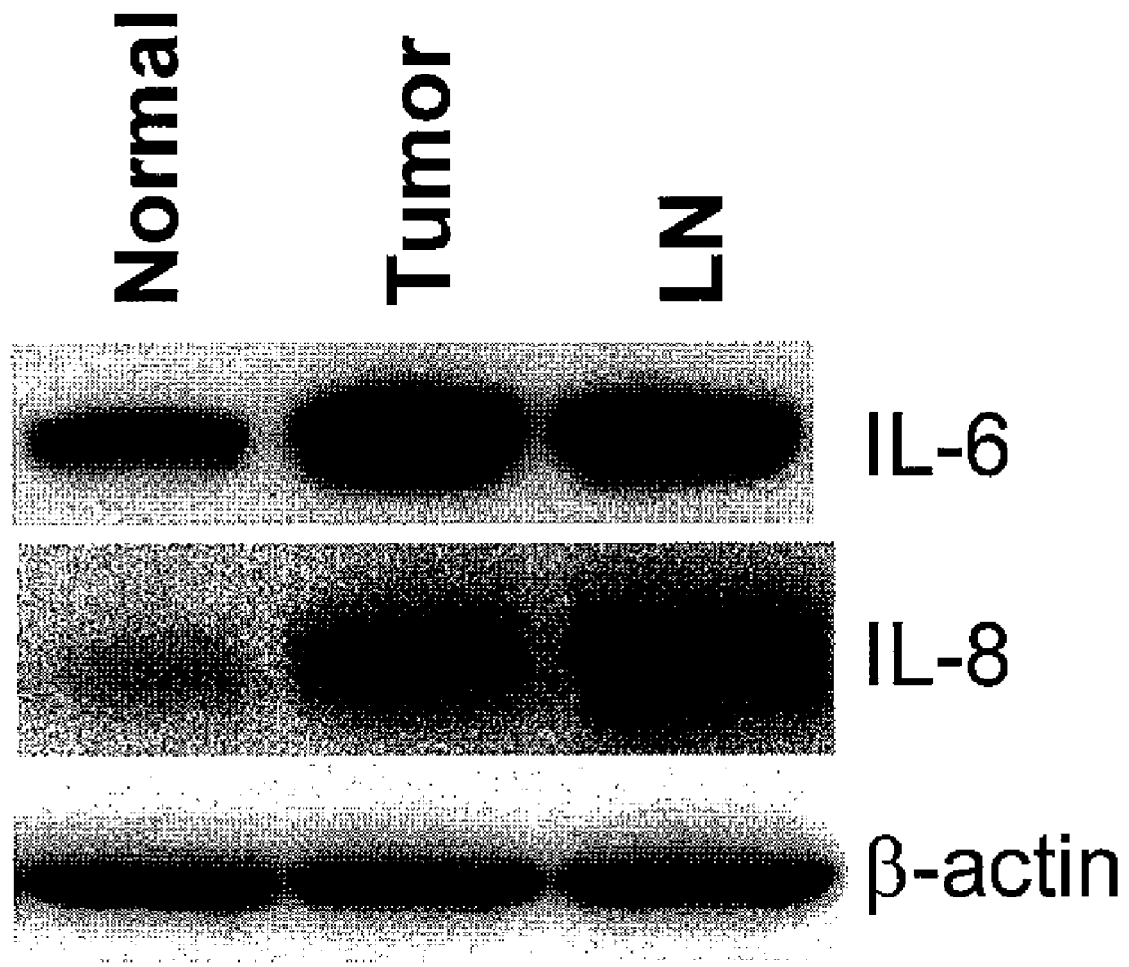
FIG. 1. Representative western blot for biomarker expression in head and neck cancer. Western blots of HNSCC lymph node biopsies (LN), tumor (T), and normal biopsies (N) were prepared using specific antibodies to IL-6, IL-8, and β-actin.

The molecular mechanisms for the progression of HNSCC cancers are not well understood and although HNSCC biomarkers have been identified, they are currently used to diagnose HNSCC in patients using biopsies from advanced stage cancers. Thus, there is a need for the development of new diagnostic tools for the early detection of HNSCC.

Biomarkers in saliva have the potential to be an important tool for early detection of HNSCC in patients, since HNSCC originates in the oral cavity, where saliva is in contact with the tumor site. The role saliva may have in the development and progression of HNSCC has been investigated. Since early detection is a key factor in the management of HNSCC and survival rate of HNSCC patients, the saliva from HNSCC patients were used in this study to determine if any biomarkers were present that may be used in the identification of early stage cancer.

The present invention provides biomarker and methods of using them to detect the development of cancer. More specifically the present invention provides biomarkers that are specific for the early detection of HNSCC.

As used herein the term "biopsy" refers to or describes tissue, cells, or fluids from a body, including but not limited to tissue in the oral cavity, saliva, serum, plasma, and the like.

A "biomarker" as used herein refers to a molecular indicator that is associated with a particular pathological or physiological state. The "biomarker" as used herein is a molecular indicator for cancer, more specifically an indicator for head and neck cancer. Examples of "biomarkers" include but or not limited to IL-1, IL-6, IL-8, VEGF, MMP-9, TGF-β, TNF-α, MMP-7, plasminogen activated (PA), uPA, IGF, INF-2 proteins, and the like. A "biomarker" of the present invention may be detected in a "biopsy."

As used herein the terms "cancer" and "cancerous" refer to or describe the physiological condition in mammals that is typically characterized by abnormal and uncontrolled cell division or cell growth. Examples of cancer include but are not limited to, carcinoma, lymphoma, blastoma, sarcoma, and leukemia. More specific examples of such cancers include breast, brain, bladder, prostate, colon, intestinal, squamous cell, lung, stomach, pancreatic, cervical, ovarian, liver, skin, colorectal, endometrial, salivary gland, kidney, thyroid, various types of head and neck cancer, and the like. More specifically, "head and neck cancer" refers to any cancer in the head or neck region of the body. Most head and neck cancers are squamous cell carcinomas, but some may be exophilic or endophilic. Examples of head and neck cancers include but are not limited to the lip, oral cavity (mouth), tongue, throat, trachea, nasal cavity, paranasal sinuses, pharynx, larynx, thyroid, salivary glands and cervical lymph nodes of the neck, and the like.

As used herein, a "subject" is preferably a human, non-human primate, cow, horse, pig, sheep, goat, dog, cat, or rodent. In all embodiments, human subjects are preferred. The "subject" may be at risk of developing head and neck cancer, may be suspected of having head and neck, or may have head and neck cancer.

As used herein, the level of expression of biomarkers can be used for the early diagnoses of cancer in a subject. In these determinations, the level of expression of the biomarker is diagnostic of cancer if the level of expression is above a control level determined for that biopsy type, but below the biomarker expression level for advanced stage cancer biopsies. The control level of expression can be determined using standard methods known to those of skill in the art. For example, a number of histologically normal biopsy samples from subjects that are clinically normal (i.e. do not have clinical signs of cancer in that tissue type) are assayed and the mean level of expression for the samples is determined. Likewise, a number of advanced stage cancer biopsy samples are assayed and the mean level of expression is determined. Biomarker expression levels of control, cancer, and sample biopsies are compared for a determination of the early diagnosis of cancer. For example, expression levels of one or more biomarkers in a sample biopsy can be about two times or more greater than the level of expression of those biomarkers in a control biopsy, but less than the biomarker expression levels of a cancer biopsy. More specifically, sample biomarker expression levels greater than about 2, 3, 4, 5, 6, 7, 8, 9, 10, 15, or 20 times or more than the level of biomarker expression in the normal control biopsy, but less than the biomarker expression levels of a cancer biopsy indicates the early diagnosis cancer in the biopsy.

Biomarker expression levels may be detected and quantified at the protein level. Methods for detecting proteins or measuring protein levels in biological samples are well known in the art. Many such methods employ antibodies (e.g., monoclonal or polyclonal antibodies) that bind specifically to target proteins. In such assays, an antibody itself or a secondary antibody that binds to it can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) familiar to those in the art can be used to enhance the sensitivity of the methodologies. Some of these protein measuring assays (e.g., ELISA or Western blot) can be applied to body fluids or to lysates of test cells and others (e.g., immunohistological methods or fluorescence flow cytometry) applied to unlysed tissues or cell suspensions. Methods of measuring the amount of a label depend on the nature of the label and are known in the art, Appropriate labels include, without limitation, radionuclides (e.g., 125I, 131I, 35S, 3H, or 32P), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties. Other applicable assays include quantitative immunoprecipitation or complement fixation assays.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

METHODS

Saliva Collection

Subjects refrained from eating, drinking, or performing oral hygiene procedures for at least one hour prior to the collection of saliva. The subject rinsed their mouth out well, without swallowing the water. Five minutes later, the subject spit into a 50 cc Falcon tube. The tube was put on ice, while more saliva was collected.

Collected saliva biopsies (1 ml) were centrifuged at 2,600 g for 15 minutes at 4° C. The supernatant was transferred to a new tube. 1 ml of Aprotinin [(10 mg/ml), 3 ml of $Na_3OV_4$ (400 mM), 10 ml of PMSF (10 mg/ml)] and protease inhibitor was added. The solution was mixed well and immediately frozen at −80° C.

Serum and Plasma Collection

For serum collection whole blood was collected into tubes that did not contain anti-coagulants. The tubes were centrifuged at 800 g for 10 minutes at room temperature under sterile conditions. The serum was removed, aliquoted into 1 ml cryogenic vials, and stored at −80° C.

For plasma collection whole blood was collected into tubes containing EDTA or sodium citrate as anti-coagulants. The tubes were centrifuged at 800 g for 10 minutes at room temperature under sterile conditions. The plasma was removed, aliquoted into 1 ml cryogenic vials, and stored at −80° C.

Western Blotting for HNSCC Biomarker Expression in Head and Neck Cancer

Western blots of biopsies from tumor, lymph node, and normal tissue were carried out to determine the relative levels of biomarker expression of IL-6 and IL-8 in those sites. β-actin was used as a control. The results show positive staining of the tumor and lymph node biopsies, while the normal biopsy shows minimal IL-6 and IL-8 staining.

Western blotting was performed by adding tissues to 0.5 ml of cold lysis buffer (50 mM Tris, pH 8, 150 mM NaCl, 1% Triton X-100, 0.5 mM EDTA, containing Halt Protease Inhibitor cocktail [Pierce, Rockford Ill.]) and homogenizing them on ice using a PowerGen 125 homogenizer (Fisher Scientific). Homogenized samples were transferred to 1.7 ml microcentrifuge tubes and centrifugated at 10,000×g for 10 min at 4° C. to clear the lysates. Protein extracts were gently removed and put into fresh tubes. Total protein was determined by Dc colorimetric assay (BioRad, Richmond, Calif.). Protein samples (25 μg protein) were fractionated on 4-20% Tris-glycine polyacrylamide gels and transferred to polyvinylidene difluoride (PVDF) membrane (Bio-Rad) by electroblotting. Membranes were blocked with 5% non-fat milk prior to incubation with primary SPK antibody at 4° C., for 16 hr. Secondary antibody (1:100,000 dilution) conjugated with horseradish peroxidase was applied for 1 hr at 25° C. The membranes were developed using the SuperSignal West Femto Maximum sensitivity chemiluminescent substrate (Pierce, Rockford, Ill.) according to the manufacturer's instructions. The same membranes were stripped and re-probed with β-actin and the chemiluminescent signal was quantitated using BioRad QuantityOne software analysis and specific proteins normalized to β-actin in each sample.

ELISA for Cancer Biomarkers

All biopsies were tested for head and neck cancer biomarkers (e.g., IL-1, IL-6, IL-8, TNF-α, and VEGF) using ELISA. Biomarker levels in saliva, serum, or plasma were determined by a solid phase double-ligand ELISA obtained from R&D Systems. A monoclonal antibody specific for the specific biomarker was pre-coated onto a micro titer plate. Standards, samples, and biomarker conjugate to horseradish peroxidase were pipetted into the wells, and any biomarker present was sandwiched by the immobilized antibody and the enzyme-linked polyclonal antibody specific for the biomarker. After removal of excess of any unbound substances and/or antibody-enzyme reagent, a substrate solution (hydrogen peroxide and chromogen tetramethylbenzidine) was added to the wells, and color was developed in proportion to the amount of biomarker bound. The color development was stopped after 30 min at room temperature, and the intensity of the color was measured at 450 nm in a microplate reader (Molecular Devices).

Biomarker Biopsy Samples

Saliva, serum, and plasma biopsies were collected from control subjects as well as subjects with cancer. Controls were divided into 4 categories: (1) healthy control, (2) control+smoker, (3) control+drinker, and (4) control+smoker+drinker. A healthy control is a subject that does not smoke, drink or have any other risk factors associated with the development of head and neck cancer. A control+smoker is a subject that is a smoker, but has not developed head and neck cancer. A control+drinker is a subject that drinks, but has not developed head and neck cancer. A control+smoker+drinker is a subject that smokes and drinks, but has not developed head and neck cancer.

Cancer biopsies included: early stage (I & II) head and neck cancer, advanced stage (III & IV) head and neck cancer, and both exophilic and endophilic tongue cancers. All biopsies (control and cancer) were tested for head and neck cancer biomarkers using ELISA.

RESULTS

Overall biomarker expression levels of IL-8 were higher in saliva than in both serum and plasma. All the control persons who did not develop cancer showed lowered expression of IL-8 in saliva compared to the patients who developed cancer. There was no difference in the levels of IL-6, IL-8, and VEGF in serum and plasma. However, in serum biopsies, the results show that a two fold increase in IL-8 and VEGF expression levels as compared to healthy control is indicative of early detection of cancer. Likewise, a 4-6 fold increase in IL-6 expression levels as compared to healthy control is indicative of early detection in serum. All other results were obtained from studies done on saliva.

TABLE I

| | Biomarker expression levels in saliva | | | | |
|---|---|---|---|---|---|
| Patient (n = 36) | IL-1 (pg/ml) | IL-6 (pg/ml) | IL-8 (pg/ml) | TNF-α (pg/ml) | VEGF (pg/ml) |
| Healthy control | 120 ± 42 | 3.4 ± .95 | 932 ± 285 | 3.9 ± 2.6 | 32 ± 8 |
| Control + Smoker | 134 ± 32 | 5.6 ± 2.5 | 1585 ± 422 | 6.6 ± 4.1 | 39 ± 10 |
| Control + Drinker | 124 ± 35 | 6.3 ± 3.1 | 1210 ± 240 | 4.6 ± 2.0 | 42 ± 12 |
| Control + Smoker + Drinker | 142 ± 40 | 8.5 ± 4.0 | 1672 ± 310 | 8.5 ± 3.0 | 55 ± 14 |
| HNC Early Stage I/II | 265 ± 26 | 154 ± 38.1 | 2450 ± 538 | 74.2 ± 24 | 120 ± 16 |
| HNC Advanced Stages III/IV | 354 ± 42.5 | 208 ± 51.6 | 3155 ± 612 | 112 ± 56.8 | 148 ± 22 |
| Tongue Cancer Endophilic | 312 ± 46 | 186 ± 38 | 2895 ± 610 | 98 ± 48 | 156 ± 31 |
| Tongue Cancer Exophilic | 210 ± 34 | 137 ± 40 | 1242 ± 408 | 38 ± 12 | 110 ± 21 |

IL-1, IL-6, IL-8 TNF-α, and VEGF expression levels that were indicative of early detection showed a two fold, twenty fold or more, two fold, fourteen fold or more, and three fold increase respectively in expression levels as compared to the healthy control (Table I).

All subjects with tongue cancer (advanced stage) expressed high levels of IL-8. However, endophilic tongue cancer showed the highest levels of IL-8 as compared to exophilic or squamous cell carcinoma tongue cancer (Table I).

Biomarkers TGF-β, tPA, and PAI also show around a 1.5 fold higher expression level as compared to the healthy control that is indicative of early detection. In addition, MMP-9 show a 1.8 fold higher expression in head and neck caner in both early and advanced stages as compared to healthy control. Thus, MMP-9 does not appear to be useful as biomarker for the early detection of cancer.

REFERENCES

1. Sankaranarayanan R, Masuyer E, Swaminathan R, Ferlay J, Whelan S. Head and neck cancer: a global perspective on epidemiology and prognosis. Anticancer Res. 1998;18: 4779-4786.
2. Greenlee R T, Murray T, Bolden S, Wingo P A. Cancer statistics, 2000. CA Cancer J Clin. 2000;50:7-33.
3. Mashberg A, Boffetta P, Winkelman R, Garfinkel L. Tobacco smoking, alcohol drinking and cancer of the oral cavity and oropharynx among U.S. veterans. Cancer. 1993; 72:1369-1375.
4. Hu S, Yu T, Xie Y, Yang Y, Li Y, Zhou X, Tsung S, Loo R R, Loo J R, Wong D T. Discovery of oral fluid biomarkers for human oral cancer by mass spectrometry. Cancer Genomics Proteomics. 2007 March-April;4(2):55-64.
5. Zimmermann B G, Park N J, Wong D T. Genomic targets in saliva. Ann NY Acad Sci. 2007 March;1098:184-91.
6. Righini C A, de Fraipont F, Timsit J F, Faure C, Brambilla E, Reyt E, Favrot M C. Tumor-specific methylation in saliva: a promising biomarker for early detection of head and neck cancer recurrence. Clin Cancer Res. Feb. 15, 2007;13(4):1179-85.

7. Ohshiro K, Rosenthal D I, Koomen J M, Streckfus C F, Chambers M, Kobayashi R, El-Naggar A K. Pre-analytic saliva processing affect proteomic results and biomarker screening of head and neck squamous carcinoma. Int J Oncol. 2007 March;30(3):743-9.
8. Chai R L, Grandis J R. Advances in molecular diagnostics and therapeutics in head and neck cancer. Curr Treat Options Oncol. 2006 January;7(1):3-11.
9. Brailo V, Vucićević-Boras V, Cekić-Arambasin A, Alajbeg I Z, Milenović A, Lukac J. The significance of salivary interleukin 6 and tumor necrosis factor alpha in patients with oral leukoplakia. Oral Oncol. 2006 April;42(4):370-3. Epub Dec. 1, 2005.
10. Vokes E E, Weichselbaum R R, Lippman S M, Hong W K. Head and neck cancer. N Engl J Med. 1993;328:184-194.
11. Boyle J O, Hakim J, Koch W, van der Riet P, Hruban R H, Roa R A, Correo R, Eby Y J, Ruppert J M, Sidransky D. The incidence of p53 mutations increases with progression of head and neck cancer. Cancer Res. 1993;53:4477-4480.
12. Brachman D G. Molecular biology of head and neck cancer. Semin Oncol. 1994;21:320-329.

What is claimed is:

1. A method for the early detection of head and neck cancer comprising:
   (a) obtaining a sample biopsy from a subject;
   (b) determining the expression level of at least one biomarker in said sample biopsy, wherein said at least one biomarker is selected from the group consisting of IL-1, IL-6, IL-8, VEGF, TGF-β, TNF-α, MMP-7, plasminogen activated (PA), uPA, IGF, and INF-2 proteins, and;
   (c) comparing the expression level of said biomarker(s) with the average expression levels of said biomarker(s) from control biopsies and advanced stage cancer biopsies;
wherein in said control biopsies are from subjects who are both smokers and drinkers but had not yet developed head and neck cancer, and wherein a determination that the level of expression of at least one biomarker in said sample is greater than the average level of expression of the same biomarker in said control biopsies, but is less than the average biomarker expression level of the cancer biopsies is indicative of the early detection of cancer in the subject.

2. The method according to claim 1, wherein said biomarker is IL-8.

3. The method according to claim 1, wherein said head and neck cancer is lip, oral cavity, tongue, throat, trachea, nasal cavity, paranasal sinuses, pharynx, larynx, thyroid, salivary glands or cervical lymph nodes of the neck.

4. The method according to claim 1, wherein said biopsy is saliva, serum, or plasma.

5. The method according to claim 1, wherein biomarker expression levels of said biopsy samples are at least two times greater than the biomarker expression levels of the control.

6. The method according to claim 1, wherein biomarker expression levels of said biopsy samples are at least five times greater than the biomarker expression levels of the control.

7. A method according to claim 1, wherein a determination that the level of expression of at least two biomarkers in said sample is greater than the level of expression of the same biomarkers in said control biopsies, but is less than the biomarker expression levels for advanced stage cancer biopsies is indicative of the early detection of cancer in the subject.

8. A method for the early detection of head and neck cancer comprising:
   (a) obtaining a sample biopsy from a subject;
   (b) determining the expression level of at least one biomarker in said sample biopsy, wherein said at least one biomarker is IL-8 and said head and neck cancer is tongue cancer, and;
   (c) comparing the expression level of said biomarker with the average expression levels of said biomarker from control biopsies and advanced stage cancer biopsies;
wherein in said control biopsies are from subjects who are both smokers and drinkers but had not yet developed head and neck cancer, and wherein a determination that the level of expression of at least one biomarker in said sample is greater than the average level of expression of the same biomarker in said control biopsies, but is less than the average biomarker expression level of the cancer biopsies is indicative of the early detection of cancer in the subject.

* * * * *